US00PP13638P29

(12) United States Plant Patent
Dümmen

(10) Patent No.: US PP13,638 P2
(45) Date of Patent: Mar. 11, 2003

(54) POINSETTIA PLANT NAMED 'DUEROSTAR'

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 10/103,949

(22) Filed: Mar. 22, 2002

(51) Int. Cl.[7] ..... A01H 5/00
(52) U.S. Cl. ..... Plt./307

(58) Field of Search ..... Plt./307, 306

*Primary Examiner*—Bruce R. Campell
*Assistant Examiner*—Michelle Kiziklya
(74) *Attorney, Agent, or Firm*—C. A. Whealy

(57) ABSTRACT

A new and distinct cultivar of Poinsettia plant named 'Dueurostar' characterized by its inflorescences with inflorescences with red-colored flower bracts; dark green-colored leaves with red purple-colored petioles; uniform and rounded plant habit; early flowering; large number of cyathia per corymb; and excellent post-production longevity.

1 Drawing Sheet

BOTANICAL CLASSIFICATION/CULTIVAR DENOMINATION

*Euphorbia pulcherrima* Willd. cultivar Dueurostar.

BACKGROUND OF THE INVENTION

The present Invention relates to a new and distinct cultivar of Poinsettia plant, botanically known as *Euphorbia pulcherrima* Willd., and hereinafter referred to by the name 'Dueurostar'.

The new Poinsettia is a product of a planned breeding program conducted by the Inventor in Rheinberg, Germany. The objective of the breeding program is to create new Poinsettia cultivars with uniform plant habit and attractive flower bract coloration.

The new Poinsettia originated from a cross-pollination made by the Inventor in 1996 of a proprietary selection of *Euphorbia pulcherrima* Willd. identified as code number 95-752-7, not patented, as the female, or seed, parent, with a proprietary selection of *Euphorbia pulcherrima* Willd. identified as code number F-06-17, not patented, as the male, or pollen, parent. The cultivar Dueurostar was discovered and selected by the Inventor as a flowering plant within the progeny of the stated cross in a controlled environment in Rheinberg, Germany in 1997. The selection of this plant was based on its attractive flower bract coloration and uniform plant habit.

Asexual reproduction of the new Poinsettia by vegetative terminal cuttings taken at Rheinberg, Germany since 1999, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Dueurostar'. These characteristics in combination distinguish 'Dueurostar' as a new and distinct cultivar:

1. Inflorescences with red-colored flower bracts.
2. Dark green-colored leaves with red purple-colored petioles.
3. Uniform and rounded plant habit.

4. Early flowering; response time, about eight weeks.
5. Large number of cyathia per corymb.
6. Excellent post-production longevity.

Compared to plants of the female parent, the selection 95-752-7, plants of the new Poinsettia have smaller flower bracts and have more cyathia per corymb. Compared to plants of the male parent, the selection F-06-17, plants of the new Poinsettia have smaller flower bracts and flower later.

Plants of the new Poinsettia can be compared to plants of the cultivar Spotlight Dark Red, not patented. In side-by-side comparisons conducted in Rheinberg, Germany, plants of the new Poinsettia differed primarily from plants of the cultivar Spotlight Dark Red in the following characteristics:

1. Plants of the new Poinsettia were more compact than plants of the cultivar Spotlight Dark Red.
2. Plants of the new Poinsettia had smaller leaves than plants of the cultivar Spotlight Dark Red.
3. Plants of the new Poinsettia had smaller flower bracts than plants of the cultivar Spotlight Dark Red.
4. Plants of the new Poinsettia had larger cyathia clusters and more cyathia per corymb than plants of the cultivar Spotlight Dark Red.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph differ slightly from the color values cited in the detailed botanical description which accurately describe the colors of the new Poinsettia.

The photograph comprises a side perspective view of a single flowering plant of 'Dueurostar' grown in a container.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Rheinberg, Germany during the winter under commercial practice in a glass-covered greenhouse with day and night temperatures about 22° C. and light levels about 4,500 lux. Single plants were grown in 13-cm pots and pinched once. Plants were flowered under natural season short day/long night conditions. Plants were about 16 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Dueurostar.

Parentage:

*Female parent.*—Proprietary selection of *Euphorbia pulcherrima* Willd. identified as code number 95-752-7, not patented.

*Male parent.*—Proprietary selection of *Euphorbia pulcherrima* Willd. identified as code number F-06-17, not patented.

Propagation:

*Type cutting.*—Vegetative terminal cuttings.

*Time to initiate roots.*—Summer: About 9 days at 22° C. Winter: About 13 days at 22° C.

*Time to develop roots.*—Summer: About 21 days at 22° C. Winter: About 28 days at 22° C.

*Root description.*—Thick, fibrous and white in color.

*Rooting habit.*—Freely branching.

Plant description:

*Plant form.*—Inverted triangle, top of plant rounded.

*Growth habit.*—Upright and uniform plant habit.

*Plant height.*—About 21 cm.

*Plant diameter or spread.*—About 38 cm.

*Lateral branch description.*—Quantity per plant: About six or seven lateral branches develop after pinching. Length: About 20 cm. Diameter: About 4 mm. Internode length: About 1 cm. Color: 137A.

*Foliage description.*—Arrangement: Alternate, single. Quantity of leaves per lateral branch: About 15. Length: About 9 cm. Width: About 6.2 cm. Shape: Mostly ovate with irregular lobing. Apex: Apiculate. Base: Obtuse. Margin: Entire with irregular lobing. Venation pattern: Pinnate. Texture, upper and lower surfaces: Glabrous, smooth. Surface: Mostly flat. Color: Young foliage, upper surface: 141B. Young foliage, lower surface: 138A. Fully expanded foliage, upper surface: 139A. Fully expanded foliage, lower surface: 138A. Venation, upper surface: 146C. Venation, lower surface: 144B. Petiole: Length: About 4.6 cm . Diameter: About 2.2 mm. Texture, upper and lower surfaces: Glabrous, smooth. Color, upper and lower surfaces: 59A.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Response time, about eight weeks.

*Post-production longevity.*—Plants of the new Poinsettia maintain good substance and bract color for about eight weeks under interior conditions and about twelve weeks under greenhouse conditions.

*Quantity of inflorescences per plant.*—One per lateral branch, about six or seven.

*Inflorescence size.*—Diameter: About 20 cm. Height (depth): About 3 cm.

*Flower bracts.*—Quantity of flower bracts per inflorescence: About 18. Length, largest bracts: About 8.6 cm. Width, largest bracts: About 5.6 cm. Shape: Mostly ovate with irregular lobing. Apex: Apiculate. Base: Obtuse. Margin: Entire with irregular lobing. Texture, upper and lower surfaces: Glabrous, velvety. Surface: Rugose. Orientation: Mostly horizontal to slightly upright. Color: Developing bracts, upper and lower surfaces: 46A. Fully developed bracts, upper surface: 46B; color fading to 46C with subsequent development. Fully developed bracts, lower surface: 46D. Venation, upper and lower surfaces: Same as lamina. Bract petiole: Length: About 1.9 cm. Diameter: About 1.7 mm. Texture, upper and lower surfaces: Glabrous, smooth. Color, upper and lower surfaces: 141B.

*Cyathia.*—Quantity of cyathia per corymb: About 15. Diameter of cyathia cluster: About 3 cm. Length: About 7 mm. Diameter: About 6 mm. Shape: Ovoid. Color, immature: 144B. Color, mature: 144A. Peduncle: Length: About 4 mm. Diameter: About 2.5 mm. Strength/aspect: Strong, curved. Color: 144B. Stamens: Quantity of stamens per cyathium: About 30. Anther shape: Oval. Anther length: About 1 mm. Anther color: 31A. Amount of pollen: Abundant. Pollen color: 14B. Pistils: Quantity of pistils per cyathium: One. Pistil length: About 1 cm. Style length: About 4 mm. Style color: 53B. Stigma color: 53A. Ovary color: 144B. Nectaries: Quantity of nectaries per cyathium. One. Length: About 5 mm. Color: 14A.

Disease/pest resistance: Resistance to pathogens and pests common to Poinsettias has not been observed on plants grown under commercial conditions.

Temperature tolerance: Plants of the new Poinsettia have been observed to tolerate temperatures from 12 to 40° C.

It is claimed:

1. A new and distinct cultivar of Poinsettia plant named 'Dueurostar', as illustrated and described.

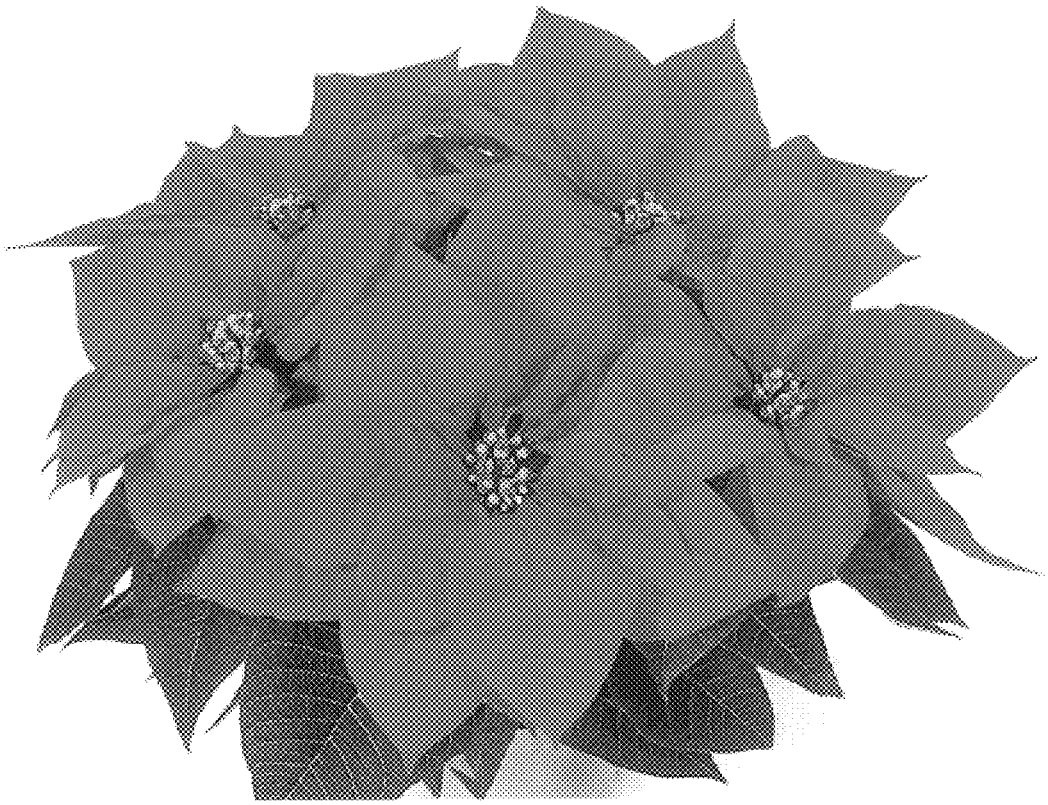

* * * * *